US008256277B2

(12) United States Patent
Khibnik et al.

(10) Patent No.: US 8,256,277 B2
(45) Date of Patent: Sep. 4, 2012

(54) GAS TURBINE ENGINE DEBRIS MONITORING ARRANGEMENT

(75) Inventors: Alexander I. Khibnik, Glastonbury, CT (US); Ravi Rajamani, West Hartford, CT (US); Rajendra K. Agrawal, S. Windsor, CT (US); Coy Bruce Wood, Ellington, CT (US)

(73) Assignee: United Technologies Corporation, Hartford, CT (US)

( * ) Notice: Subject to any disclaimer, the term of this patent is extended or adjusted under 35 U.S.C. 154(b) by 490 days.

(21) Appl. No.: 12/482,605

(22) Filed: Jun. 11, 2009

(65) Prior Publication Data

US 2010/0313639 A1 Dec. 16, 2010

(51) Int. Cl.
*G01M 15/14* (2006.01)
(52) U.S. Cl. .................................................. 73/112.01
(58) Field of Classification Search ............... 73/112.01, 73/112.03, 112.04, 112.05
See application file for complete search history.

(56) References Cited

U.S. PATENT DOCUMENTS

| 4,212,190 | A | 7/1980 | Coover et al. |
| 4,296,628 | A | 10/1981 | Mast |
| 4,528,844 | A | 7/1985 | Couch |
| 4,584,531 | A | 4/1986 | Couch |
| 4,607,228 | A | 8/1986 | Reif |
| 4,888,948 | A | 12/1989 | Fisher et al. |
| 4,926,120 | A | 5/1990 | Veronesi et al. |
| 5,041,856 | A | 8/1991 | Veronesi et al. |
| 5,070,722 | A | 12/1991 | Hawman et al. |
| 5,760,298 | A | 6/1998 | Fisher et al. |
| 6,668,655 | B2 | 12/2003 | Harrold et al. |
| 7,213,475 | B2 | 5/2007 | Coghill |
| 2008/0016971 | A1 | 1/2008 | Bunce et al. |
| 2009/0014245 | A1 | 1/2009 | Shevchenko et al. |
| 2009/0112519 | A1* | 4/2009 | Novis et al. ................... 702/183 |
| 2010/0287907 | A1* | 11/2010 | Agrawal et al. ............ 60/39.091 |
| 2010/0288034 | A1* | 11/2010 | Agrawal et al. ............ 73/112.01 |
| 2010/0292905 | A1* | 11/2010 | Agrawal et al. ................ 701/100 |
| 2011/0179763 | A1* | 7/2011 | Rajamani et al. .......... 60/39.092 |

OTHER PUBLICATIONS

<http://www.ni.com/signalconditioning/whatis.htm, National Instruments, What is Signal Conditioning.
Gas Path Debris Monitoring for F-35 Joint Strike Fighter Propulsion System PHM, IEEEAC paper #1100, Version 2, Jan. 4, 2006, Honor Powrie, Ari Novis.
PHM Sensor Implementation in the Real World—a Status Report, IEEEAC paper #1106, Version 3, Oct. 19, 2005, Ari Novis, Honor Powrie.
Gas Path Debris Monitoring—A 21st Century PHM Tool, IEEE Aerospace Conference, 2000.

* cited by examiner

*Primary Examiner* — Eric S McCall
(74) *Attorney, Agent, or Firm* — Carlson, Gaskey & Olds PC

(57) ABSTRACT

An example method of controlling gas turbine engine debris monitoring sensors includes detecting debris carried by air moving through an engine using at least first and second debris sensors, and processing signals from both the first and second debris sensors using a common signal conditioning unit. Another example method of monitoring gas turbine engine debris includes configuring at least one first debris sensor to detect debris carried by airflow moving through a first portion of an engine and configuring at least one second debris sensor to detect debris carried by airflow moving though a second portion of the engine. The method alternates between using the first debris sensor to detect debris and using the second debris sensor to detect debris.

18 Claims, 4 Drawing Sheets

GAS TURBINE ENGINE DEBRIS MONITORING ARRANGEMENT

BACKGROUND

This application relates generally to monitoring gas turbine engine debris, and more particularly, to detecting debris using different debris sensors.

Gas turbine engines are known and typically include multiple sections, such as a fan section, a compression section, a combustor section, a turbine section, and an exhaust nozzle section. During stable operation, the fan section moves air into the engine. The air is compressed as the air flows through the compression section. The compressed air is then mixed with fuel and combusted in the combustor section. Products of the combustion expand to rotatably drive the engine.

Gas turbine engines operate in various environments. Some environments include debris, such as sand and stones, which can move into the engine with the air. As known, debris can undesirably accelerate wear and erosion of the engine's components. Engines often utilize inlet debris monitoring systems to detect and monitor particles of debris entering the engine. Other types of debris monitoring systems monitor debris in other areas of the engine, For example, an exit debris monitoring system monitors debris exiting areas of the engine. These systems typically include one or more debris sensors within or in front of the fan section of the engine. The debris sensors detect debris entering the engine by sensing the electrostatic charge of debris. The inlet debris monitoring system compiles the detection information for monitoring purposes as is known art.

The sensitivity of the debris sensors to the electrostatic charges of the debris depends in part on the size and exposed surface of the debris sensor. For example, smaller diameter ringed debris sensors are more sensitive to electrostatic charges than larger diameter ringed debris sensors, and axially wider ringed debris sensors are more sensitive to electrostatic charges than axially narrower ringed debris sensors. Button type sensors are another example type of debris sensor. Using debris sensors that are too sensitive, or sensors that are not sensitive enough, can complicate distinguishing electrostatic charges of the debris from other electrostatic charges. Example complications include signal saturation, which could result from using sensors having large sensor surfacing areas to detect large amounts of dense particulate, such as a cloud of sand or water.

In the prior art, each debris sensor communicates with a signal conditioning unit dedicated to that debris sensor. That is, the number of signal condition units is the same as the number of debris sensors, which presents a bulky and complex arrangement. After detecting an electrostatic charge from debris, the debris sensor communicates a signal to the signal conditioning unit, which filters and digitizes the signal. The filtered and digitized signals are provided to the inlet debris monitoring system, which can then determine the quantity and rate of debris entering the engine.

SUMMARY

An example method of controlling gas turbine engine debris monitoring sensors includes detecting debris carried by air moving through an engine using at least first and second debris sensors, and processing signals from both the first and second debris sensors using a common signal conditioning unit.

Another example method of monitoring gas turbine engine debris includes configuring at least one first debris sensor to detect debris carried by airflow moving through a first portion of an engine and configuring at least one second debris sensor to detect debris carried by airflow moving though a second portion of the engine. The method alternates between using the first debris sensor to detect debris and using the second debris sensor to detect debris An example gas turbine engine monitoring arrangement includes at least one first sensor configured to detect debris in an engine and at least one second sensor configured to detect debris in the engine. A single signal conditioning unit is configured to condition signals from both of the at least one first sensor and the at least one second sensor.

These and other features of the example disclosure can be best understood from the following specification and drawings, the following of which is a brief description.

DETAILED DESCRIPTION

Figure 1:
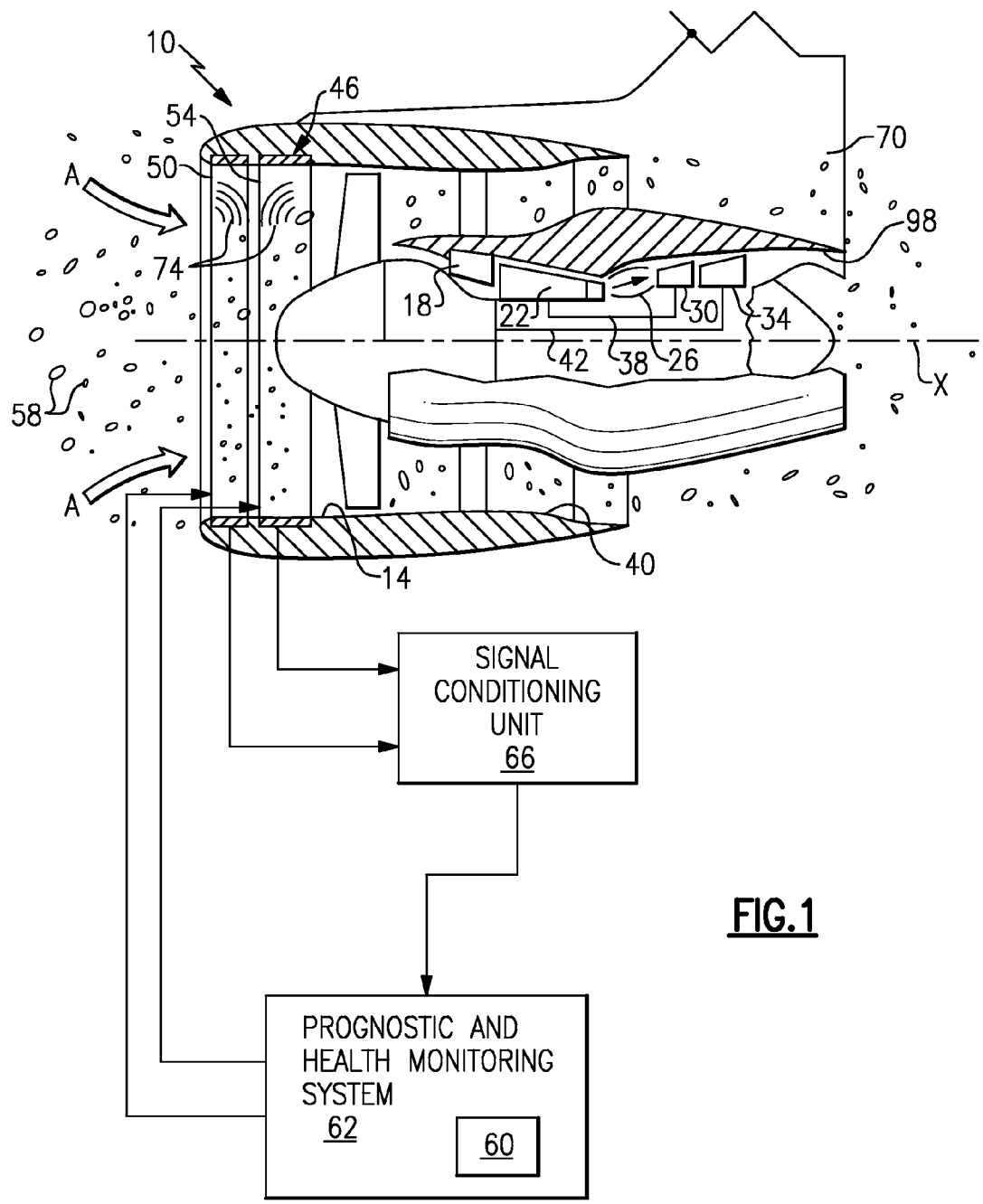
FIG. 1 shows an example gas turbine engine and an example monitoring arrangement.

FIG. 1 schematically illustrates an example gas turbine engine 10 including (in serial flow communication) a fan section 14, a low-pressure compressor 18, a high-pressure compressor 22, a combustor 26, a high-pressure turbine 30, and a low-pressure turbine 34. The gas turbine engine 10 is circumferentially disposed about an engine centerline X.

During operation, air A is pulled into the gas turbine engine 10 by the fan section 14. Some of the air A moves to a core of the engine 10 and is pressurized by the compressors 18 and 22, mixed with fuel, and burned in the combustor 26. The turbines 30 and 34 extract energy from the hot combustion gases flowing from the combustor 26. Air A that does not move through the core of the engine 10 moves through a bypass flow path 40.

In a two-spool design, the high-pressure turbine 30 utilizes the extracted energy from the hot combustion gases to power the high-pressure compressor 22 through a high speed shaft 38, and the low-pressure turbine 34 utilizes the extracted energy from the hot combustion gases to power the low-pressure compressor 18 and the fan section 14 through a low speed shaft 42. The examples described in this disclosure are not limited to the two-spool engine architecture described, however, and may be used in other architectures, such as a single-spool axial design, a three-spool axial design, and still other architectures.

A debris sensor system 46 is mounted to the fan section 14 of the engine 10 and is configured to detect the debris 58 carried by the air A pulled into the gas turbine engine 10 by the fan section 14. In this example, the debris sensor system 46 includes a first ringed debris sensor 50 and a second ringed debris sensor 54. Using more than one sensor within the debris sensor system 46 facilitates improved sensitivity to debris 58, validating signatures of the debris 58, tracking the path of debris 58 through the engine 10, and measuring parameters of the debris 58.

Figure 2:
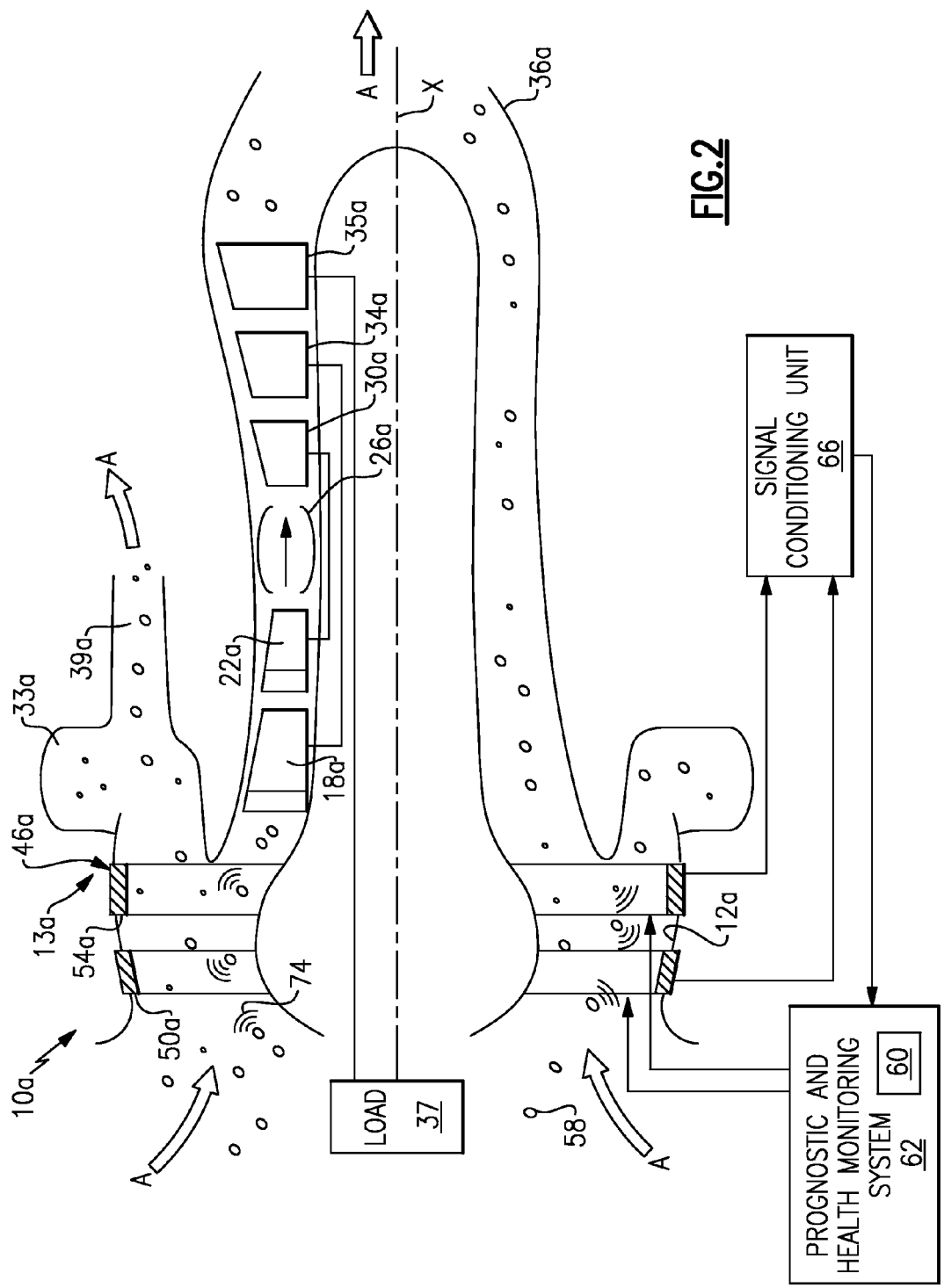
FIG. 2 shows a partial schematic view of an example turboshaft gas turbine engine and the component assessment system.

The examples described are also not limited to the turbofan gas turbine engine 10. For example, FIG. 2 schematically illustrates an example turboshaft gas turbine engine 10*a* including (in serial flow communication) an inlet section 12*a*, an inlet particle separator section 13*a*, a low-pressure compressor 18*a*, a high-pressure compressor 22*a*, a combustor 26*a*, a high-pressure turbine 30*a*, a low-pressure turbine 34*a* and a power turbine section 35*a*. The inlet particle separator section 13*a* includes an inlet particle separator scroll 33*a* and a blower 39*a* as is known. A bypass flow of air moves through the blower 39*a* in this example. In this example, the inlet particle separator section 13*a* includes a debris sensor system 46*a* having a first ringed debris sensor 50*a* and a second ringed debris sensor 54*a*.

The turbines 30*a* and 34*a* of the gas turbine engine 10*a* extract energy from the hot combustion gases flowing from the combustor 26*a*. The residual energy is expanded through the power turbine section 35*a* to produce output power that drives an external load 37, such as helicopter rotor system. Air is exhausted from the engine 10*a* at the exhaust nozzle section 36*a*. There are various types of engines, in addition to the turbofan gas turbine engine 10 of FIG. 1 and the turboshaft gas turbine engine 10*a*, that could benefit from the examples disclosed herein, which are not limited to the designs shown. That is, there are various types of engines that could utilize the examples disclosed herein, which are not limited to the design shown.

A controller portion 60 of a prognostic and health monitoring system 62 is configured to selectively initiate detecting the debris 58 using the first ringed debris sensor 50, the second ringed debris sensor 54, or both. In this example, the prognostic and health monitoring system 62 is mounted to an aircraft 70 that is propelled by the gas turbine engine 10. Other examples may include other debris sensor rings in addition to the first ringed debris sensor 50 and the second ringed debris sensor.

A signal conditioning unit 66 processes signals from the first ringed debris sensor 50, the second ringed debris sensor 54, or both, depending on how the controller portion 60 has initiated detection of the debris 58. The signal conditioning unit 66 can be configured to receive input from the first ringed debris sensor 50, the second ringed debris sensor 54, or both, depending on signal strength from that sensor. The prognostic and health monitoring system 62 indicates the presence of the debris 58 using the processed and digitized signals from the signal conditioning unit 66. Processing the signals with the signal conditioning unit 66 includes digitizing and adjusting the signals for use by a prognostic and health monitoring system 62. Other examples of the signal processing unit comprise a signal interface unit or smart signal conditioning unit, which integrates signal conditioning with signal processing for vibration monitoring systems in environments such as production plants as is known. Other examples of processing include amplifying the signals, calibrating the signals, and correlating the signals.

The first ringed debris sensor 50 and the second ringed sensor 54 detect electrostatic charges 74 from the debris 58 passing through the first ringed debris sensor 50. If the electrostatic charges 74 from the debris 58 are detected, the debris sensor system 46 sends a signal to the signal conditioning unit 66 indicating the presence of the debris 58. Although this example only shows some of the debris 58 having the electrostatic charges 74 for clarity, nearly all of the debris 58 provide some electrostatic charge that is detectable by one or both of the first ringed debris sensor 50 and the second ringed debris sensor 54. Examples of detecting include sending a signal to the controller portion 60, announcing an event to a pilot or maintenance worker associated with the aircraft 70, measuring parameters of the debris 58 for the purposes of damage prognosis.

Figure 3:
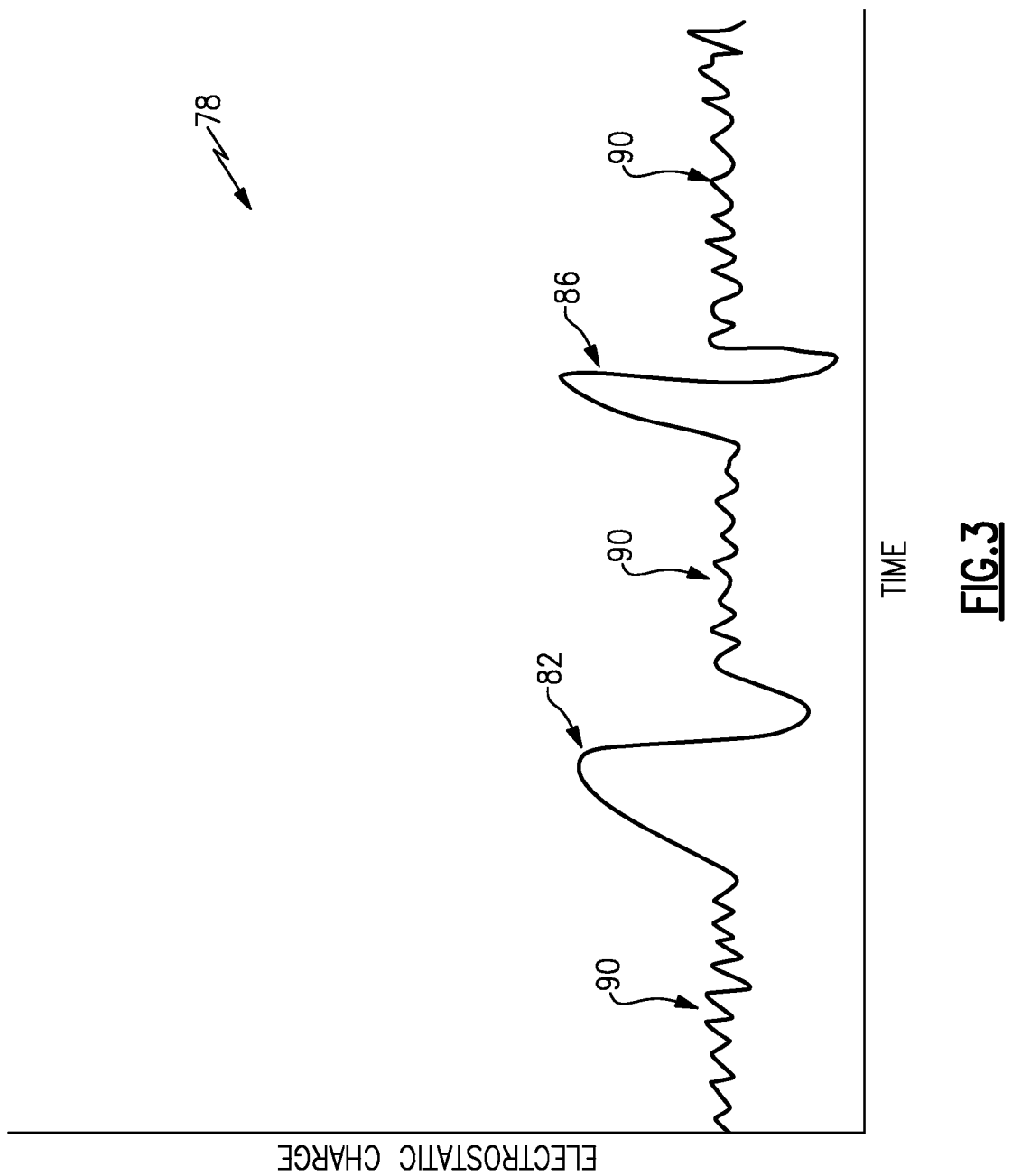
FIG. 3 shows an example graphical output from the FIG. 1 monitoring arrangement.

Referring to FIG. 3 with continuing reference to FIGS. 1 and 2, the electrostatic charges 74 from a particle of the debris 58 is represented on an electrostatic charge graph 78 of the first ringed debris sensor 50 as a pulse 82. The electrostatic charge graph 78 has another pulse 86, which indicates the presence of another particle of the debris 58 that is moving through the ringed debris sensor 50. The prognostic and health monitoring system 62 estimates the size of the debris 58 based on the amplitude and width of the pulses 82 and 86, for example.

The pulses 82 and 86 extend beyond noise portions 90 of the electrostatic charge graph 78. As can be appreciated, increasing the signal-to-noise ratio for the electrostatic charge graph 78 is desirable, for example, to clarify differences between the pulse 82, which indicates the debris 58, and the noise portions 90, which do not indicate the debris 58. The signal-to-noise ratio thus represents the difference between noise portions 90 of the electrostatic charge graph 78 and the peaks of the pulses 82 and 86.

Figure 4:
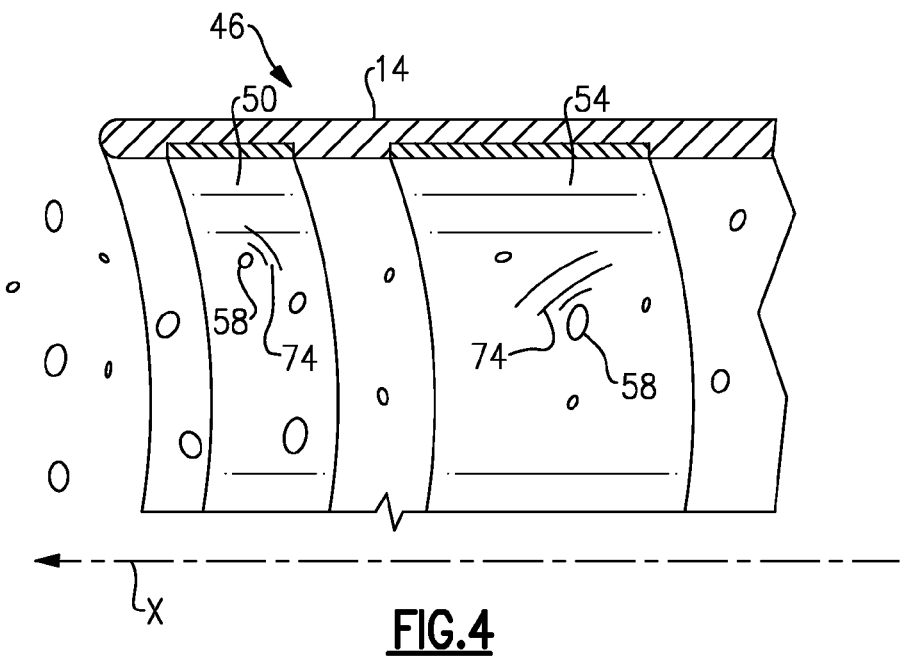
FIG. 4 shows a close-up partial view of the FIG. 1 gas turbine engine.
Figure 5:
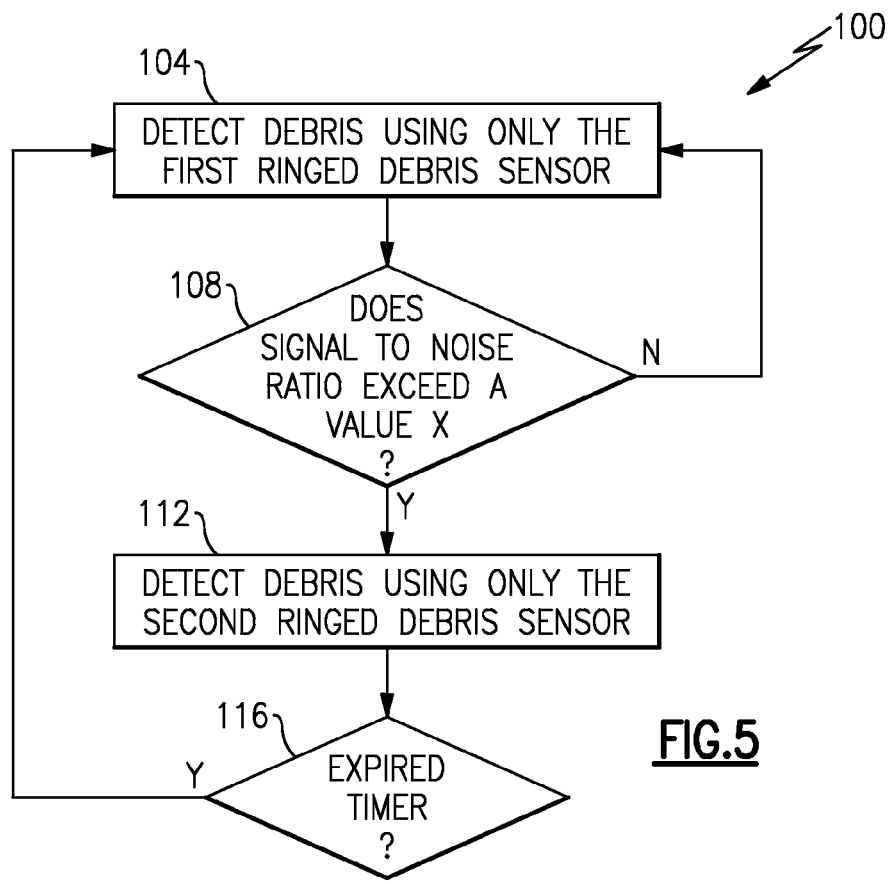
FIG. 5 shows the flow of an example method of monitoring the FIG. 1 gas turbine engine.

Referring to FIGS. 4 and 5 with continuing reference to FIGS. 1-3, in this example, the first ringed debris sensor 50 is axially narrower than the second ringed debris sensor 54 and has less surface area available for monitoring the debris 58. The first ringed debris sensor 50 is thus less sensitive to overall electrostatic charges 74 from the debris 58 than the second ringed debris sensor 54 but provides a higher signal to noise ratio of electrostatic charges 74 that are detected. In other examples, relative differences between the radial diameters of the ringed debris sensors 50 and the second ringed debris sensor 54 result in varied sensitivity to electrostatic charges 74. The sensors of the debris sensor system 46 having varied radial diameters may be positioned in different areas of the engine 10, such as the bypass flow path 40 or an exhaust stream 98, for example.

Other examples variables for altering the sensitivity to debris of the first ringed debris sensor 50 relative to the second debris sensor 54 include changing the environment of the sensor within the engine 10, which can vary the vibration environment or the noise environment adjacent the sensors or adjacent harnesses associate with sensor communications. Still other examples include changing the sensor material, the sensor orientation, designing gaps or other variations within the individual sensors, or altering how the sensors mount to the engine 10 (attached using glue, with insulating materials, etc. The first ringed debris sensor 50 and the second ringed debris sensor 54 are typically made of a conducting material, such as aluminum.

In this example, the controller portion 60 of the prognostic and health monitoring system 62 is configured to selectively initiate detecting the debris 58 using the first ringed debris sensor 50, the second ringed debris sensor 54, or both. Accordingly, the controller portion 60 can initiate a particular combination of sensors within the debris sensor system 46 to desirably achieve relatively high signal-to-noise ratios between the pulses 82 and 86, and the noise portions 90 of the electrostatic charge graph 78.

The controller portion 60 can also initiate a particular combination of sensors within the debris sensor system 46 to desirably achieve a higher sensitivity to electrostatic charges 74. For example, if the debris 58 entering the engine 10 have relatively low electrostatic charges 74, the controller portion 60 initiates detection of the debris 58 using only the second ringed debris sensor 54, which is more sensitive to electrostatic charges 74 than the first ringed debris sensor 50. By contrast, if the debris 58 entering the engine 10 have a relatively high electrostatic charges 74, the controller portion 60 initiates detection of the debris 58 using only the first ringed debris sensor 50, which is less sensitive to electrostatic charges 74 than the second ringed debris sensor 54. In some examples, the controller portion 60 initiates detection of the debris 58 using both the first ringed debris sensor 50 and the second ringed debris sensor 54.

As known, the size of the electrostatic charges 74 from the debris 58 are related to the size and type of the debris 58 and also to the mixture of debris 58 of different sizes. Examples of the debris 58 having relatively low electrostatic charges 74 include isolated bits of fine sand or bugs. Examples of the debris 58 having relatively high electrostatic charges 74 include gravel and pebbles or a dust storm carrying large amounts of fine sand. Measured charge is a function of the surface area of the sensors 50 and 54, the debris 58 distance from the sensors 50 and 54 and exposure time (which is a function of the velocity of the debris). Sequentially monitoring some types of debris 58 is often appropriate because the debris 58 are relatively consistent as they move through the engine 10, a sandstorm for example. Thus, sequential monitoring will not result in loss of information.

In one example, the speed of the debris 58 moving through the engine 10 is determined by measuring electrostatic charges 74 of debris 58 using the first ringed debris sensor 50 and then switching to measure electrostatic charges 74 from the same debris 58 or cloud of debris using the second ringed debris sensor 54. Alternatively, if both the first ringed debris sensor 50 and the second ringed debris sensor 54 are simultaneously detecting debris 58, an interval between the pulses can indicate the speed of the debris 58. A person skilled in the art and having the benefit of this disclosure would be able to determine the speed of the debris 58 moving through the fan section 14 using these measurements.

In examples where the debris sensor system 46 monitors the debris 58 in the fan section 14 and the bypass flow path 40, the amount of the debris 58 moving through these areas can be determined from the monitoring. For example, subtracting the amount of the debris 58 moving through the bypass flow path 40 from the amount of the debris 58 moving into the engine 10 facilitates the amount of the debris 58 moving through the low pressure compressor 18, the high pressure compressor 22, and other areas of the core of the engine 10. In such examples, even though the debris 58 are monitored by the debris sensor system 46 sequentially, little information is lost because the debris 58 moving through the engine 10 remain relatively consistent. In such an example, the sensors in the fan section 14 and the bypass flow path 40 may have same sensitivity to electrostatic charges 74.

An example method 100 of controlling the debris sensor system 46 minimizes the number sensors needed for detecting the debris 58. Initially, at a step 104, the controller portion 60 initiates detection of the debris 58 using only the first ringed debris sensor 50. The method 100 then determines at a step 108 whether a signal-to-noise ratio for the pulse 82, for example, exceeds a threshold value. In one example, the threshold value for the signal to noise ratio is about 5. The signal is not saturated if the signal-to-noise ratio exceeds the threshold value. Thus, if the signal-to-noise ratio exceeds the threshold value, the controller portion 60 continues to initiate detection of the debris 58 using only first ringed debris sensor 50. If, however, the signal-to-noise ratio does not exceed the threshold value, the controller portion 60 initiates detection using the second ringed debris sensor 54 instead of the first ringed debris sensor 50 at a step 112. As previously described, the second ringed debris sensor 54 is more sensitive to electrostatic charges 74 than the first ringed debris sensor 50. At a step 116, the controller portion 60 returns to initiating detection of the debris 58 using only the first ringed debris sensor 50 at the step 104 after expiration of a certain time period. In another example, the method 100 returns to the step 104 after the aircraft 10 reaches a certain altitude.

Varying the combinations of the sensors within the debris sensor system 46 monitoring for debris 58 facilitates maximizing the signal-to-noise ratio for the pulse 82, which can enhance debris detection rates and minimize false readings of debris 58. Further, because the example prognostic and health monitoring system 62 using the method 100 alternates between receiving signals from the first ringed debris sensor 50 and the second ringed debris sensor 54, only the signal conditioning unit 66 is required to process signals in some examples. In the prior art, additional signal conditioning units are required.

Features of the disclosed examples include adjusting the detection sensitivity of a system that detects gas turbine engine debris to improved debris detection rates and reliability. Another feature includes eliminating signal conditioning units within an aircraft.

Still other features of the disclosed examples include a debris monitoring system arrangement where n debris sensors ($n>=2$) are served by m ($1<=m<n$) signal conditioning units, a signal conditioning unit for debris monitoring that can be programmed and/or controlled to accept and condition signals from more than one debris sensor, a signal conditioning unit with inputs from more than one sensor where weight of sensor inputs can be adjusted based on measured debris conditions and or engine operating conditions.

Example adjustments include: attenuating or turning off inputs from one or several sensors to prevent debris signal saturation and ensure signal range required for signal conversion; amplifying or turning on input from one or several services sensors to increase sensitivity of measured signal to the presence of potentially damaging debris; turning acquisition of one sensor signal on/off and turning another sensor signal acquisition in the opposite direction to modify (increase or decrease) sensitivity of measured signal to debris based on required inputs to the debris monitoring system; switching from a less sensitive sensor to a more sensitive sensor to improve detection function accuracy and robustness for smaller size discrete debris or low rate particulate debris; switching from a more sensitive sensor to a less sensitive sensor to improve detection function accuracy and robustness for larger size discrete debris or higher rate particulate debris; switching between sensors or modifying relative weighting of sensors in response to a detection of a debris event start, a detection of debris event end, or a controller signal indicating power modulation of Inlet Particle Separator (IPS); switching between sensors or modifying input weights according to a schedule; acquiring a signal from sensors in different parts of the engine sequentially (sequentially acquired signals may be processed sequentially or in parallel); switching between sensors or modifying input weights in a manner allowing or improving monitoring debris path through the engine and ultimately enabling accurate debris monitoring system damage assessment; and switching between sensors or modifying input weights in a manner allowing or improving debris monitoring system function to accurately determine debris flow rate and debris composition, particularly in the case of particulate debris.

Although a preferred embodiment has been disclosed, a worker of ordinary skill in this art would recognize that certain modifications, such as adding additional sensors, would come within the scope of this invention. For that reason, the following claims should be studied to determine the true scope and content of this invention.

We claim:

1. A method of monitoring gas turbine engine debris comprising:
    configuring at least one first debris sensor to detect debris carried by airflow moving through a first portion of an engine;
    configuring at least one second debris sensor to detect debris carried by airflow moving though a second portion of the engine;
    alternating between using the first debris sensor to detect debris, the second debris sensor to detect debris, or both; and
    including measuring the speed of debris carried by the airflow by detecting the debris using the at least one first debris sensor and the at least one second debris sensor.

2. The method of claim 1 including alternating between the first debris sensor and the second debris sensor in response to a type of debris.

3. The method of claim 1 wherein the alternating includes alternating between using exclusively the first debris sensor to detect debris and exclusively using the second debris sensor to detect debris.

4. The method of claim 1, wherein both the first and second debris sensor are located axially forward a fan of the engine.

5. The method of claim 1 wherein a fan section of the engine comprises the first portion, and a bypass flow path of the engine comprises the second portion.

6. The method of claim 5 including subtracting an amount of debris in the bypass flow path from an amount of debris in the fan section to determine an amount of debris entering a core of the engine.

7. A method of controlling gas turbine engine debris monitoring sensors comprising:
    detecting debris carried by air moving through an engine using at least first and second debris sensors; and
    conditioning signals from both the first and second debris sensors that are at different axial locations within the engine using a common signal conditioning unit, wherein at least one of the plurality of debris sensors has a different electrostatic charge sensitivity than another of the plurality of debris sensors.

8. The method of claim 7 including sequentially processing the signals.

9. The method of claim 7 wherein the processing comprises amplifying features of the signal.

10. The method of claim 7, wherein both the first and second debris sensor are located in an inlet section of the engine.

11. The method of claim 7 including the first debris sensor in an inlet section of the engine and a second debris sensor in a bypass flow path of the engine.

12. The method of claim 11 including subtracting a measured amount of debris in the bypass flow path from a measured amount of debris in the inlet section to determine an amount of debris entering a core of the engine.

13. A gas turbine engine monitoring arrangement comprising:
    at least one first sensor configured to detect debris at a first axial location in an engine;
    at least one second sensor configured to detect debris at a second, different axial location in the engine; and
    a single signal conditioning unit configured to condition signals from both of the at least one first sensor and the at least one second sensor, wherein both the first and second debris sensor are located within a fan section of the engine.

14. The arrangement of claim 13 wherein the at least one first sensor, the at least one second sensor, or both comprise a ring sensor circumferentially disposed about an axis of the engine.

15. The arrangement of claim 13 wherein the at least one first sensor is positioned within a fan section of the engine and the at least one second sensor is in a bypass flow duct of the engine.

16. The arrangement of claim 13 including a controller configured to selectively initiate debris detection using exclusively the at least one first sensor, exclusively the at least one second sensor, or both.

17. The arrangement of claim 13 wherein the first sensor has an exposed surface area that is different than the second sensor.

18. The arrangement of claim 13 where the single signal conditioning unit conditions signals from the at least one first sensor during a first time period, and from the at least one second sensor during a second time period different than the first time period.

* * * * *